United States Patent [19]

Yamada et al.

[11] 4,310,487

[45] Jan. 12, 1982

[54] AUTOMATIC ANALYZER FOR COMBUSTIBLE GAS IN OIL

[75] Inventors: Mitsuhiro Yamada; Hirokazu Katayama, both c/o Kansai Electric Power Company Incorporated, Sohgo Gityutsu Kenkyusho, No. 1, Nakohji Ichinotsubo, Amagasaki-shi, Hygo-ken, Japan; Toshitsugu Ishii; Yoshihiro Makino, both of Akoh, Japan; Masashi Kamio, Amagasaki, Japan

[73] Assignees: Mitsubishi Denki Kabushiki Kaisha, Tokyo; Mitsuhiro Yamada; Hirokazu Katayama, both of Hyogo, all of Japan

[21] Appl. No.: 134,073

[22] Filed: Mar. 26, 1980

[30] Foreign Application Priority Data

Mar. 26, 1979 [JP] Japan .................................. 54/35322

[51] Int. Cl.³ ............................................ G01N 33/28
[52] U.S. Cl. ................................. 422/68; 23/230 HC; 422/80; 422/94
[58] Field of Search ...................... 23/230 M, 230 HC; 422/68, 80, 94

[56] References Cited

U.S. PATENT DOCUMENTS 3,920,396  11/1975  Schuy ............................ 422/68 X
4,208,372  6/1980  Huber ............................ 422/68 X Primary Examiner—Ronald Serwin
Attorney, Agent, or Firm—Oblon, Fisher, Spivak, McClelland & Maier

[57] ABSTRACT

An automatic analyzer for measuring a combustible gas dissolved in an oil such as an insulating oil in a transformer includes a gas desorbing device, a gas discharger and a combustible gas detector. The oil is sampled and the gas dissolved in the oil is desorbed by bubbling air and a mixed gas of the desorbed gas and air is fed into a bellows type gas discharger and the concentration of the combustible gas is measured by the combustible gas detector.

5 Claims, 4 Drawing Figures

AUTOMATIC ANALYZER FOR COMBUSTIBLE GAS IN OIL

BACKGROUND OF THE INVENTION

1. Field of the Invention

The present invention relates to an automatic analyzer for a combustible gas dissolved in an oil such as an insulating oil in a transformer which is in an operation.

2. Description of the Prior Art

When a concentration of a combustible gas in an oil is measured, a sample oil is sampled through a valve equipped at the bottom of the transformer (1) as shown in FIGS. 1 (A), (B) and (C) into a sample vessel for the oil (2). A predetermined quantity of the sampled oil is charged into Torricelli's desorbing device (3). The gas dissolved in the oil is desorbed and a part of the desorbed gas is sampled as a test gas into a syringe (4). The test gas in the syringe (4) is fed into a combustible gas detector (5) to measure the concentration thereof.

In the conventional system, the operation from the sampling of the sample oil to the measurement of the concentration of the combustible gas is operated by a manual operation. A gas desorbing device using mercury has been mainly employed. A gas desorbing device which is convenient for using in various places has not been developed. The operation from the sampling of the oil to the measurement of the concentration of the combustible gas is not continuous, whereby a dead capacity of equipments is large to cause a great loss of the sample of the gas. The desorbing device is to desorb the combustible gas from the oil by forming a vacuum space on the surface of the oil. Therefore, when the gas content in the oil is not enough, the gas used for the measurement is not satisfactorily obtained. These are serious disadvantages.

SUMMARY OF THE INVENTION

It is an object of the present invention to provide an automatic analyzer for measuring a concentration of a combustible gas dissolved in an oil.

The automatic analyzer for a combustible gas of the present invention comprises a gas desorbing device wherein the oil is sampled into a vessel and a gas is fed into the vessel to desorb the dissolved gas dissolved in the oil; a gas discharger which is connected to the vessel to discharge the desorbed gas out of the vessel; and a combustible gas detector which detects the concentration of the combustible gas in the desorbed gas, whereby the operation can be continuously carried out in a speedy manner and the combustible gas can be easily sampled, even though the quantity of the gas in the oil is small. These are significant advantages in the practical operation.

DETAILED DESCRIPTION OF THE PREFERRED EMBODIMENTS

Figure 1A:
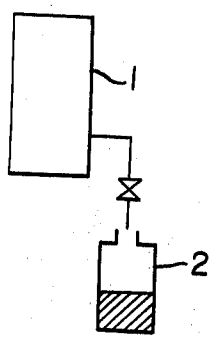
FIGS. 1A, 1B and 1C are schematic views of the conventional apparatus for measuring a concentration of the combustible gas dissolved in the oil.
Figure 1B:
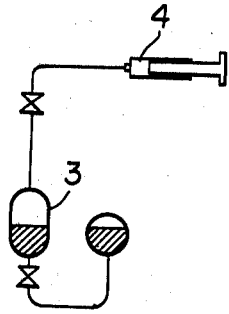
Figure 1C:
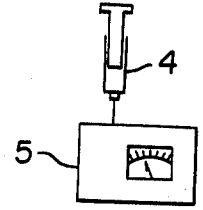

The present invention has been proposed to overcome the disadvantages of the conventional apparatus. The purpose of the present invention is to provide the automatic analyzer for the combustible gas dissolved in the oil which can continuously operate in a speedy manner and can easily sample the gas even though the quantity of thegas dissolved in the oil is small. The automatic analyzer comprises a gas desorbing device wherein the sample of the oil is sampled into the vessel and the gas is fed into the vessel to desorb the dissolved gas dissolved in the oil; the gas discharger which is connected to the vessel to discharge the desorbed gas out of the vessel; and the combustible gas detector which detects the concentration of the combustible gas in the desorbed gas.

Referring to the drawing, one embodiment of the automatic analyzer for the combustible gas dissolved in the oil of the present invention will be described.

Figure 2:
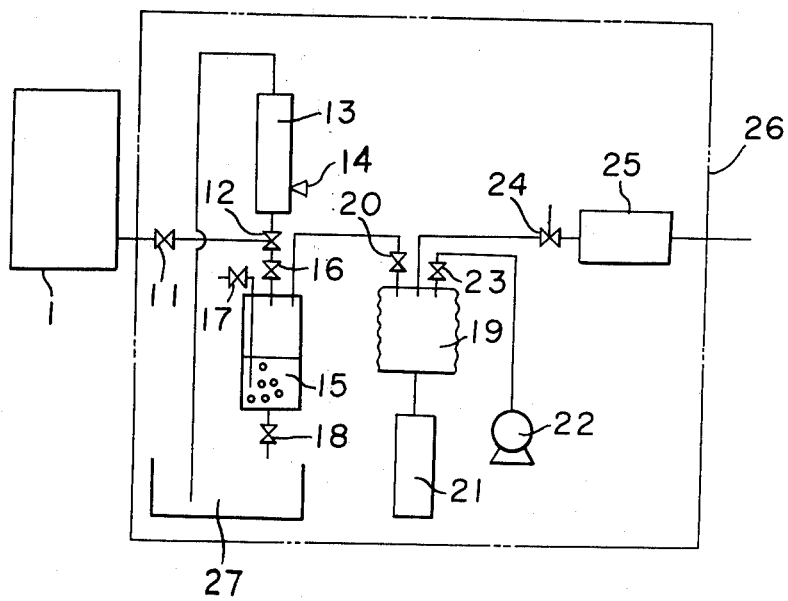
FIG. 2 is a schematic view of one embodiment of an automatic analyzer for a combustible gas in oil of the present invention.

In FIG. 2, the reference (11) designates an electromagnetic valve for sampling the sample oil from a transformer (1); (12) designates a three way electromagnetic valve which separates the flow of the sample oil sampled by the electromagnetic valve (11), into two ways by the switching operation. The reference numeral (13) designates a sampled oil messcylinder, one end of which is connected to one of the three way electromagnetic valve (12) and the other end of which is connected to a waste oil vessel (27). The reference numeral (14) designates an oil level detector which is equipped with the sampled oil messcylinder (13); (15) designates a bubbling vessel which is connected through an electromagnetic valve (16) to the other one of the three way electromagnetic valve (12) and is connected through an electromagnetic valve (17) to the outer portion of the vessel and the bottom of the bubbling vessel is connected through an electromagnetic valve (18) to the waste oil vessel (27); (19) designates a bellows type gas discharger which is connected through an electromagnetic valve (20) to the bubbling vessel (15) and is driven by a bellows driver (21) and is connected through an electromagnetic valve (23) to a vacuum pump (22); (24) designates a three way electromagnetic valve which is switched to connect to the bellows type gas discharger (19) and the combustible gas detector (25) or the bellows type gas discharger (19) and atmosphere respectively; and (26) designates a case for holding these equipments in one unit.

The operation of the embodiment having the above-mentioned structure will be illustrated.

In the sampling of the oil from the transformer (1), the electromagnetic valves (17), (18) are closed and the electromagnetic valves (16), (20), (23) are opened. The three way electromagnetic valves (12), (24) are respectively connected to the transformer (1) and the sampled oil messcylinder (13) and to the atmosphere and the combustible gas detector (25). The bellows type gas discharger (19) is extended to be the maximum length by the bellows driver (21) and the system is evacuated by the vacuum pump (22). When the system is evacuated, the electromagnetic valves (16), (23) are closed and the electromagnetic valve (11) is opened to feed the oil from the transformer into the sampled oil messcylinder (13) to overflow the oil from the messcylinder (13) into the waste oil vessel (27) and then, the electromagnetic valve (11) is closed. The three way electromagnetic valve (12) is connected to the sampled oil messcylinder (13) and the bubbling vessel (15). The electromagnetic valve (16) is opened to transfer the oil down as the sample into the bubbling vessel (15). When the level of the oil in the sampled oil messcylinder (13) is decreased to the oil level detector (14,) the electromagnetic valve (16) is closed. When the electromagnetic valve (17) is opened, air is fed into the oil and is further fed into the bellows type gas discharger (19) together with the extracted gas dissolved in the oil. The movement of air is continued until the pressure in the bellows type gas discharger (19) reaches atmospheric pressure. When it reaches atmospheric pressure, the electromagnetic valve (20) is closed and the electromagnetic valve (18) is opened. The current is fed to the combustible gas detector (25) and clean air is sucked from atmosphere through the three way electromagnetic valve (24) by a pump (not shown) and the zero level of the combustible gas detector (25) is adjusted, and then, the combustible gas detector (25) is connected through the three way electromagnetic valve (24) to the bellows type gas discharger (19) and simultaneously, the electromagnetic valve (23) is opened and the bellows gas discharger (19) is contracted at a constant velocity by the bellows driver (21) to feed the sample gas into the combustible gas detector (24) so as to measure the concentration of the combustible gas.

In this embodiment, the insulating oil in the transformer (1) is used as the sample oil. It is not limited in use to the insulating oil. Air is fed into the bubbling vessel (15) to generate the bubbling. A similar effect is attained by using an inert gas for the bubbling. It is also possible to use a piston type, pressurizing pump type and vacuum pump type discharger instead of the bellows type gas discharger (19).

As stated above, in accordance with the present invention, the automatic analyzer for a combustible gas comprises the gas desorbing device wherein the oil is sampled into the vessel and the gas is fed into the vessel to desorb the dissolved gas dissolved in the oil; a gas discharger which is connected to the vessel to discharge the the desorbed gas out of the vessel; and the combustible gas detector which detects the concentration of the combustible gas in the desorbed gas whereby the operation can be continuously carried out in a speedy manner and the combustible gas can be easily sampled, even though the quantity of the gas in the oil is small. The advantages in the practical use are remarkable.

We claim:

1. An automatic analyzer for a combustible gas comprising:

a gas desorbing device comprising a cylinder for receiving oil and a bubbling vessel wherein an oil to be sampled is fed from said cylinder into said vessel and a gas dissolved in said oil;

a gas discharger connected to said bubbling vessel to discharge said desorbed gas out of said vessel; and a combustible gas detector which detects a concentration of said combustible gas in said desorbed gas.

2. An automatic analyzer for a combustible gas according to claim 1 wherein said gas discharger is a bellows type gas discharger.

3. An automatic analyzer for a combustible gas according to claim 1 further comprising a case wherein said gas desorbing device, said gas discharger and said combustible gas detector are mounted in said case.

4. An automatic analyzer for a combustible gas according to claim 1, further comprising a three way valve interconnecting said cylinder and said bubbling vessel.

5. An automatic analyzer for a combustible gas according to claim 4, further comprising a three way valve interconnecting said gas discharger and said gas detector and communicating to atmosphere.

* * * * *